US009352077B2

(12) United States Patent
Arndt et al.

(10) Patent No.: US 9,352,077 B2
(45) Date of Patent: *May 31, 2016

(54) ROTATIONAL PUMP AND METHODS FOR CONTROLLING ROTATIONAL PUMPS

(71) Applicant: Berlin Heart GmbH, Berlin (DE)

(72) Inventors: Andreas Arndt, Berlin (DE); Kurt Graichen, Berlin (DE); Peter Nüsser, Kleinmachnow (DE)

(73) Assignee: Berlin Heart GmbH, Berlin (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/290,863

(22) Filed: May 29, 2014

(65) Prior Publication Data

US 2014/0343352 A1    Nov. 20, 2014

Related U.S. Application Data

(63) Continuation of application No. 12/671,945, filed as application No. PCT/EP2008/006510 on Aug. 1, 2008, now Pat. No. 8,747,293.

(60) Provisional application No. 60/953,772, filed on Aug. 3, 2007.

(30) Foreign Application Priority Data

Aug. 3, 2007    (EP) ...................................... 07075665

(51) Int. Cl.
*A61M 1/10*    (2006.01)
*A61M 1/12*    (2006.01)

(52) U.S. Cl.
CPC ............. *A61M 1/1086* (2013.01); *A61M 1/122* (2014.02); *A61M 1/101* (2013.01); *A61M 2205/3344* (2013.01)

(58) Field of Classification Search
CPC ... A61M 1/101; A61M 1/1086; A61M 1/122; A61M 1/125
USPC .................... 417/18, 20, 22, 42, 43, 44.1, 53; 600/16, 17
See application file for complete search history.

(56) References Cited

U.S. PATENT DOCUMENTS

| 5,888,242 A | 3/1999 | Antaki et al. |
| 6,066,086 A | 5/2000 | Antaki et al. |

(Continued)

FOREIGN PATENT DOCUMENTS

| EP | 1 046 403 A1 | 10/2000 |
| EP | 1 354 606 A1 | 10/2003 |

OTHER PUBLICATIONS

International Preliminary Report on Patentability and Written Opinion, dated Feb. 9, 2010, pp. 1-9, International Application No. PCT/EP2008/006510, The International Bureau of WIPO.

*Primary Examiner* — Peter J Bertheaud
(74) *Attorney, Agent, or Firm* — Brinks Gilson & Lione

(57) ABSTRACT

A rotational pump capable of running at a rotational speed (n) having a system for direct or indirect measurement of pressure difference or flow rate across the pump, wherein a control system is designed to calculate an index of pulsatility (PI) of the pressure difference or flow rate, estimating the gradient of PI with respect to the rotational speed (dPI/dn) and regulating the dPI/dn to a pre-defined set-point or regulating the pump in a way that the dPI/dn is minimal.

12 Claims, 14 Drawing Sheets

(56) References Cited

U.S. PATENT DOCUMENTS

| | | | |
|---|---|---|---|
| 6,991,595 B2 * | 1/2006 | Burke et al. ................ 600/17 |
| 7,963,905 B2 | 6/2011 | Salmonsen et al. |
| 2005/0131271 A1 | 6/2005 | Benkowski et al. |
| 2007/0142923 A1 | 6/2007 | Ayre et al. |

* cited by examiner

ROTATIONAL PUMP AND METHODS FOR CONTROLLING ROTATIONAL PUMPS

CROSS-REFERENCE TO RELATED APPLICATIONS

This application is a continuation of, and claims priority under 35 USC §120 to, U.S. Non-Provisional patent application Ser. No. 12/671,945, entitled "ROTATIONAL PUMP AND METHODS FOR CONTROLLING ROTATIONAL PUMPS," which is a 371 nationalization of PCT/EP2008/006510 filed Jan. 1, 2008, the entire contents of which are incorporated herein by reference, and which, in turn, claims priority under 35 USC §119(e) to U.S. Provisional Application 60/953,772 filed Aug. 3, 2007 and priority under 35 USC §119 to European Patent Application 07075665.5 filed Aug. 3, 2007.

BACKGROUND

The invention relates to rotational pumps and methods for controlling rotational pumps.

Although research in the field of physiological control of rotary pumps dates back to the early 1990s rotary blood pumps (RBP) used as left ventricular assist devices (LVADs) were initially operated at a constant rotational speed which was adjusted individually according to the patient's need. Early clinical experience clearly showed that ventricular collapse and excessive suction are serious hazards related with the operation of these pumps.

These rotational blood pumps are implanted into a human body. The inlet of the blood pump is normally connectable to the left ventricle of the human, the outlet of a pump is connectable to the aorta, downstream of the aortic valve (AoV).

RBPs used as LVADs are often required to deliver the maximum possible flow rate. This may be the case in the early post-op period or when seriously impaired end-organ function requires optimum perfusion. Several approaches are known that attempt to meet this requirement by operating the pump near the collapse point of the LV, where the flow rate is as high as possible. On the other hand, it is known that excessive unloading of the LV may impair the pumping performance of the right ventricle because of the septum shift. Furthermore, it is hypothesized that the alteration of the natural flow path of the LV in combination with the greatly reduced LV wall movement due to full unloading causes recirculation and stasis inside the LV cavity. To date, there is only anecdotal evidence of thrombus formation in the LV, but atrial fibrillation can be considered to be a comparable situation in which thrombo-embolic complications are a well-known problem. Additionally, full unloading is contra-indicated for patients whose hearts may recover under assist and who are potential candidates for weaning. These facts strongly indicate that it may be better not always to operate the RBP at the point of maximum flow rate but also at a point where unloading is only partial, LV volume and LV wall movement are not minimal and at the optimum achievable washout of the LV cavity and where the aortic valve opens at least occasionally.

It is the object of the invention to provide a rotational blood pump and a control method which finds and adjusts the optimum operating point under all conceivable physiological situations without requiring the attention of a physician. An operating point may be optimal with regard to the therapeutic objectives mentioned above and which can be classified into two cases: Full Assist (FA)—maximum support with closed AoV but sufficient safety margin to avoid suction, and Partial Assist (PA)—moderate support at the transition region between the opening of the AoV and a permanently-closed AoV with near-physiological LV volume, better LV washout and moderate LV loading.

SUMMARY

A rotational pump, especially a rotational blood pump capable of running at a rotational speed (n) having a system for direct or indirect measurement of pressure difference or flow rate across the pump, wherein a control system is designed to calculate an index of pulsatility (PI) of the pressure difference or flow rate, estimating the gradient of PI with respect to the rotational speed (GPI=dPI/dn) and regulating the GPI to a pre-defined set-point or regulating the pump in a way that the GPI is minimal.

A method to control a rotational blood pump, characterized by direct or indirect measurement of the pressure difference or flow rate across the pump, calculating an index of pulsatility (PI) of the pressure difference or flow rate, estimating the gradient of PI with respect to rotational speed (n) GPI and regulating the GPI to a pre-defined set-point or regulating the pump in a way that the GPI is minimal.

The pump might be used in different technical fields. It is advisable to implant the rotational blood pump into a human or animal body wherein the inlet of the rotational pump is to be connected with the left ventricle of the heart and the outlet of the pump is to be connected with the aorta, downstream of the aortic valve. It is also conceivable to implant the pump as a right ventricular assist device (RVAD), where the inlet of the pump is connected to the right ventricle and the outlet is connected to the pulmonary artery, downstream of the pulmonary valve. For simplicity, only the LVAD case shall be described below, without limiting the invention to LVAD.

A control strategy for rotary blood pumps meeting different user-selectable control objectives is proposed: maximum support with the highest feasible flow rate versus medium support with maximum ventricular washout and controlled opening of the aortic valve. A pulsatility index (PI) is calculated from the pressure difference, which might be deduced from the axial thrust measured by a magnetic bearing of the pump or by other means. Alternatively the flow rate through the pump may serve as the basis for calculating the PI. The gradient of PI with respect to pump speed (GPI) might be estimated via on-line system identification. The outer loop of a cascaded controller regulates GPI to a reference value satisfying the selected control objective. The inner loop controls the PI to a reference value set by the outer loop. Adverse pumping states such as suction and regurgitation can be detected on the basis of the GPI estimates and corrected by the controller. A lumped-parameter computer model of the assisted circulation may be used to simulate variations of ventricular contractility, pulmonary venous pressure and aortic pressure. The performance of the outer control loop may be demonstrated by transitions between the two control modes. Fast reaction of the inner loop may be tested by stepwise reduction of venous return. For maximum support, a low PI may be maintained without inducing ventricular collapse. For maximum washout, the pump may work at a high PI in the transition region between the opening and the permanently closed aortic valve. The cascaded control of GPI and PI is able to meet different control objectives.

The gradient GPI is extracted from the system dynamics which is identified by an on-line parameter estimation method.

The set-point of GPI may be selected in such a way that the pump operates in the transitional phase in between an opening an a closed aortic valve, this phase being at the transition point between partial and total assist.

The GPI might be regulated to the set-point by a cascaded controller with an inner and an outer loop. The outer loop may comprise a feedback control loop that keeps the GPI to its set-point and whose output is a reference value for the PI.

An inner feedback control loop may keep the actual PI close to the reference value for PI by calculating a reference value for the rotational speed.

The minimum of GPI maybe maintained by a cascaded controller with an inner and an outer loop.

The outer loop may comprise a feedback control loop that keeps the GPI to its minimum value and whose output is a reference value for the PI.

The inner feedback control loop of the controller may keep the actual PI close to the reference value for PI by calculation a reference value for the rotational speed.

The rotational speed may be temporarily reduced from the operating point by a fixed value to allow the aortic valve (or pulmonary valve respectively) to open in systole.

The parameters of the inner feedback control loop may be adapted to the estimated system dynamics.

BRIEF DESCRIPTION OF THE DRAWINGS

Embodiments of the invention are described in the following.

DESCRIPTION OF PREFERRED EMBODIMENTS

Figure 1:
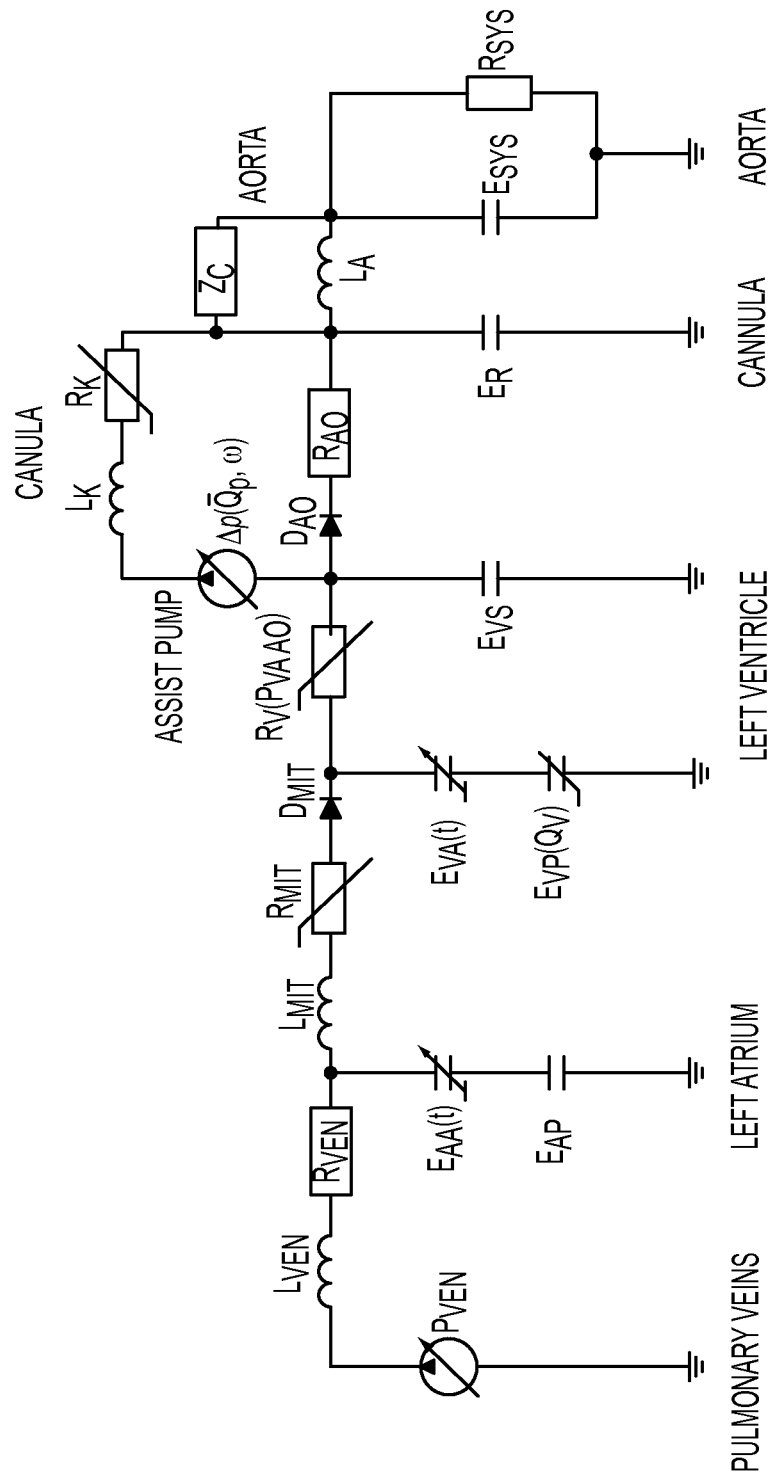
FIG. 1 is a lumped-parameter simulation model, $p_{ven}$, pulmonary venous pressure; $L_{ven}$, $R_{ven}$, inertia and resistance of pulmonary vein; $E_{aa}$, $E_{ap}$, active and passive left atrial elastance; $L_{mit}$, $R_{mit}$, inertia and resistance of mitral valve; $D_{mit}$, mitral valve; $E_{va}$, $E_{vp}$, active and passive left ventricular elastance; $R_v$, left ventricular viscous element; $E_{vs}$, left ventricular series elastance; $D_{ao}$, aortic valve; $R_{ao}$, resistance of aortic valve; $Z_c$, $L_a$, $E_{sys}$, $R_{sys}$, 4-element windkessel model of aorta with characteristic impedance, inertia, elastance and systemic resistance of the aorta; p, pressure difference generated by the assist pump; $L_k$, $R_k$, $E_k$, inertia, resistance and elastance of the cannulas.

A lumped-parameter computer simulation model was developed to design and test the control algorithm (FIG. 1). The model consists of the pulmonary venous vasculature, left atrium (LA), LV, aorta and assist pump. The pulmonary veins, represented by inertia $L_{ven}$ and viscous element $R_{ven}$, are supplied by the pulmonary venous pressure $p_{ven}$. The LV was modeled by an E(t)-R model incorporating an active time-varying elastance $E_{va}(t)$, a pressure-dependent viscous element $R_v$ and series elastance $E_{vs}$. The exponential relationship between passive filling pressure and filling volume $Q_v$ is accounted for by the passive elastance $E_{vp}(Q_v)$. The LA is modeled using a simpler E(t) model with active elastance $E_{aa}(t)$ and constant passive elastance $E_{ap}$ according to a linear passive pressure-volume relationship. The open mitral valve is simulated by inertia $L_{mit}$ and viscous term $R_{mit}$, whereas the open aortic valve has only a viscous term $R_{ao}$. Both valves, when dosed, are simulated by infinite resistances. The aorta is represented by a 4-element windkessel model consisting of the characteristic impedance $Z_c$ and inertia La of the proximal aorta, elastance $E_{sys}$ and peripheral resistance $R_{sys}$. A model of the INCOR axial-flow blood pump (Berlin Heart GmbH, Berlin, Germany) was used as an assist pump model. The pump characteristic $\Delta p = f(\dot{Q}_p, \omega)$ is approximated by a multiple regression model with pressure difference Δp, pump flow rate $\dot{Q}_p$ and pump speed ω. The cannulas of the INCOR system are represented by an inertial term $L_k$, viscous term $R_k$ and elastic term $E_k$. The whole network can be described by a set of 9 non-linear first order differential equations with state vector $$x = [\dot{Q}_{ven} p_{ap} \dot{Q}_{mit} p_{vp} p_{vs} \dot{Q}_p p_{ao} Q_L p_{sys}]^T, \quad (1)$$

where $\dot{Q}_{ven}$ is the pulmonary venous flow, $p_{ap}$ the passive LA pressure, $\dot{Q}_{mit}$ the trans-mitral flow, $p_{vp}$ the passive LV pressure, $p_{vs}$ the auxobaric LV pressure, $\dot{Q}_p$ the pump flow, $p_{ao}$ the proximal aortic pressure, $Q_L$ the proximal aortic flow and $p_{sys}$ is the systemic arterial pressure. The control vector is $$u = [p_{ven} E_{aa} E_{va} \omega]^T. \quad (2)$$

No output vector shall be defined for simulation purposes, as all states can be monitored.

The elastance functions $E_{aa}(t)$ and $E_{va}(t)$ resemble the atrial and ventricular activation functions. They can be normalized with respect to time and magnitude with max $(E_N(t_N))=1$ for $t_N=1$. The normalized elastance function was approximated by a hybrid cosine function:

$$E_N(t_N) = 0.5 \begin{cases} 1 - \cos(\pi t_N) & \text{for } 0 \leq t_N \leq 1 \\ 1 + \cos\left(\dfrac{t_N - 1}{t_{end} - 1}\right) & \text{for } 1 \leq t_N \leq t_{end}. \end{cases} \quad (3)$$

with $t_{end}$=15, a relaxation time between 50 and 80 ms can be achieved for auxobaric contraction.

Occlusion of the input cannula due to negative left ventricular pressure (LVP) was implemented by setting $R_v = \infty$ for LVP<1 mmHg. A small hysteresis reproduces the characteristic suction limit cycles observed in patients.

Figure 2:
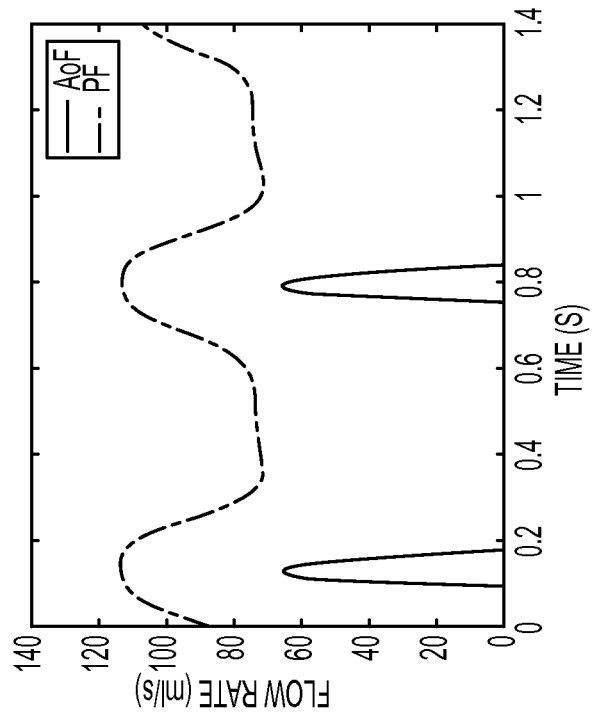
FIG. 2 shows a simulated pressure waveforms for aortic pressure AoP=85 mmHg, contractility $E_{max}$=1 mmHg/ml, pulmonary venous pressure $p_{ven}$=8 mmHg and pump speed ω=7500 rpm. LVP, left ventricular pressure; LAP, left atrial pressure; AoP, aortic pressure; Δp, pressure difference across assist pump; AoF, aortic flow; PF, pump flow.
Figure 2:
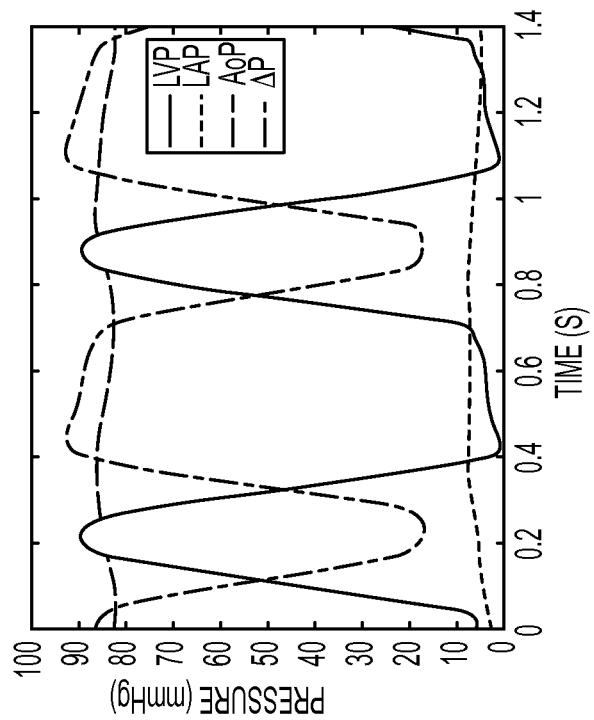

The model was implemented with Matlab/Simulink (The MathWorks, Natick, Mass., USA). All physiological parameters have been set according to literature data and the pressure and flow waveforms have been validated with literature data as well. The pressure difference waveform was compared to patient data from the INCOR patient database. FIG. 2 shows the pressure and flow waveforms for simulation of an assisted pathological left ventricle.

Note that the input $\omega$ is the only one of the 4 elements of control vector u directly accessible in clinical use, whereas $p_{ven}$, $E_{aa}$ and $E_{va}$ are unknown. The output vector contains only the measurable variables pump flow and pressure difference $$y=[\dot{Q}_p, \Delta p]^T. \quad (4)$$

If the system were to be linearized at a certain operating point, it would not be completely observable because most elements of state matrix A and most of the control signal values are unknown. The proposed control strategy is based on regulating the LV pressure, or correspondingly, the filling volume $Q_v$, which, on account of the nonlinearities, is reflected by the PI of the pressure difference signal for a given contractility $E_{max}$ and afterload AoP. The PI is filtered out of the pressure difference signal (provided by the magnetic bearing of the pump) by low-pass filtering (LP) of the magnitude (abs) of the high-pass filtered (HP) $\Delta p$ signal:

$$PI=LP\{abs[HP(\Delta p)]\}. \quad (5)$$

Figure 3:
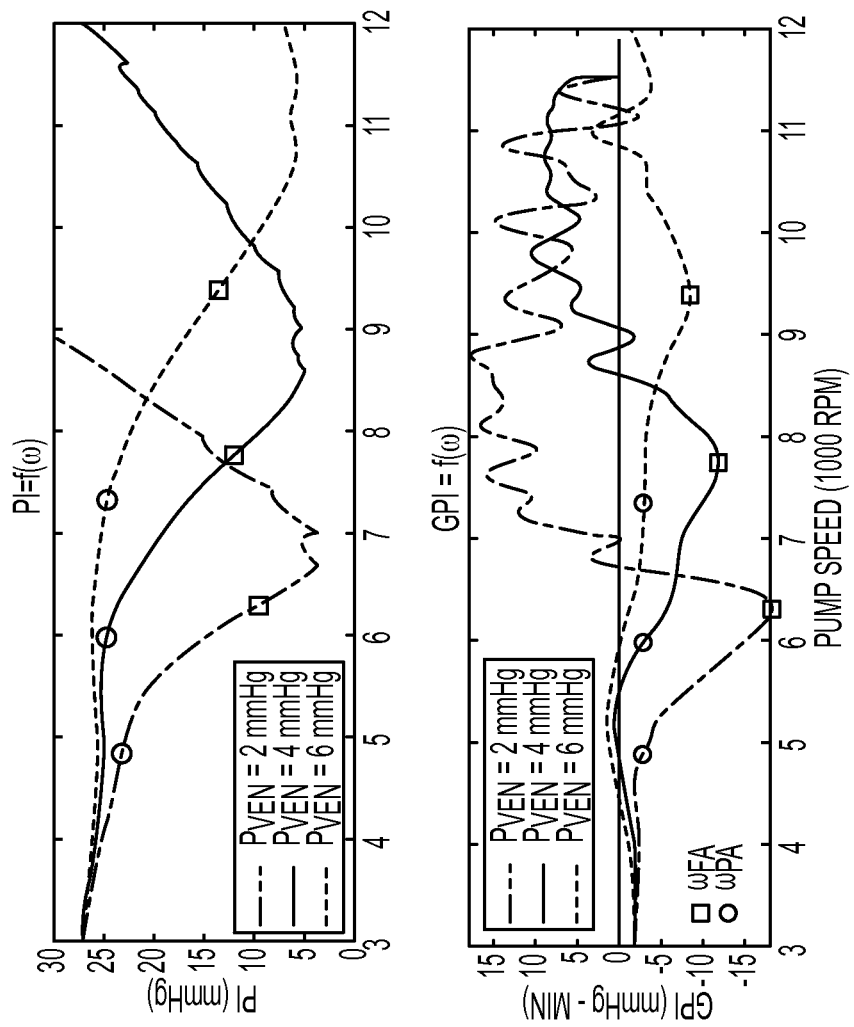
FIG. 3 shows the dependence of pulsatility index PI and its gradient GPI on pump speed ω for different pulmonary venous pressures $p_{ven}$.
Figure 4:
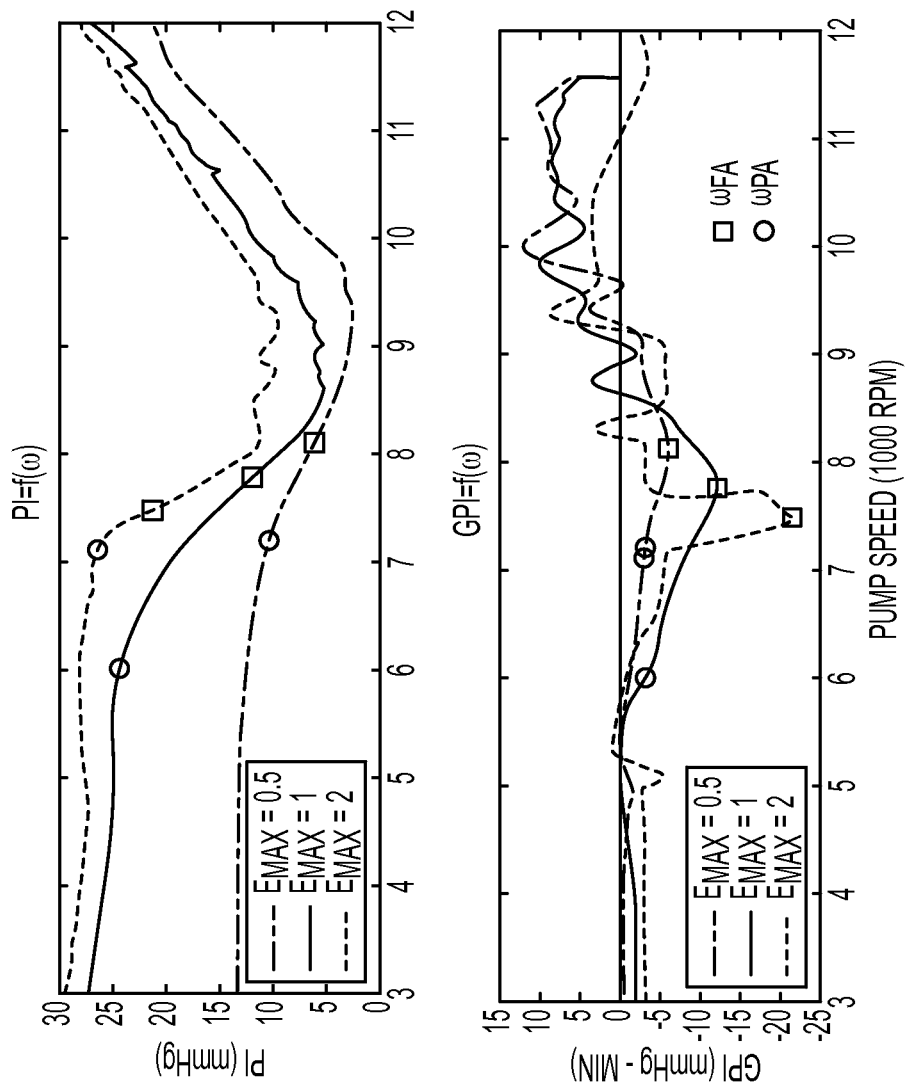
FIG. 4 shows the dependence of pulsatility index PI and its gradient GPI on pump speed ω for different contractility levels $E_{max}$.
Figure 5:
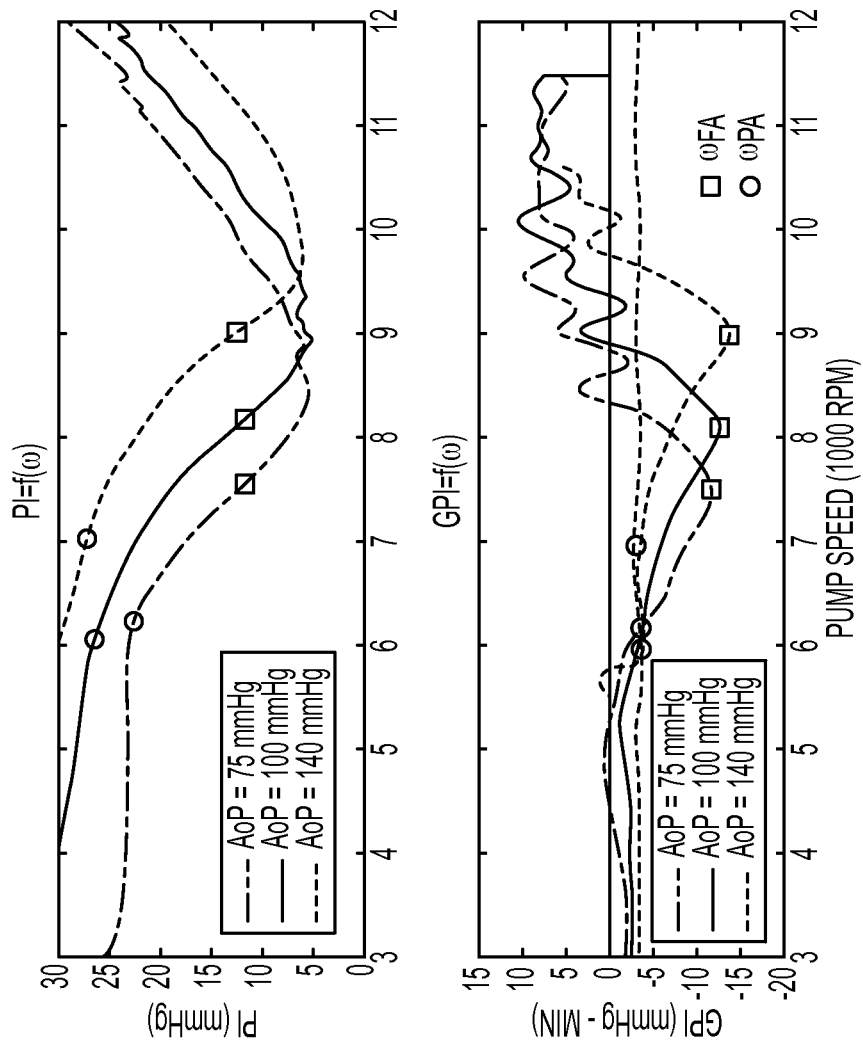
FIG. 5 shows the dependence of pulsatility index PI and its gradient GPI on Pump speed ω for different levels of mean aortic pressure AoP.

The dependence of PI on $\omega$ for different filling pressures is shown in the top part of FIG. 3. For $\omega<\omega_{PA}$, PI remains almost constant at a high level because the AoV opens in every systole. For $\omega_{PA} \leq \omega \leq \omega_S$, the AoV remains permanently closed and PI decreases with increasing $\omega$. When the minimum is reached, suction starts due to a low LV end-diastolic volume and low LV end-diastolic pressure. For $\omega>\omega_S$ PI increases again, caused by the positive suction spikes of the pressure difference. It can be seen that higher filling pressures shift the PI curves to higher $\omega$ values. Independently of $p_{ven}$, optimal operating points can be assigned: for PA mode this is $\omega_{PA}$, whereas the maximum negative slope of the PI, marked as $\omega_{FA}$, was selected for FA mode. At $\omega_{FA}$, a high pump flow is achieved with a sufficient safety margin with respect to suction. To determine both these operating points, the gradient of PI with respect to $\omega(GPI=\delta PI/\delta\omega)$ was calculated off-line (FIG. 3, bottom). If the operating points $\omega_{PA}$ are transferred to the GPI, it can be seen that these points are all located at a small negative value of GPI, regardless of $p_{ven}$. The points $\omega_{FA}$ are located at the minimum of GPI. This relation is also true for different levels of contractility (FIG. 4) and afterload (FIG. 5). The control task consists of determining and tracking these operating points on-line.

Figure 6:
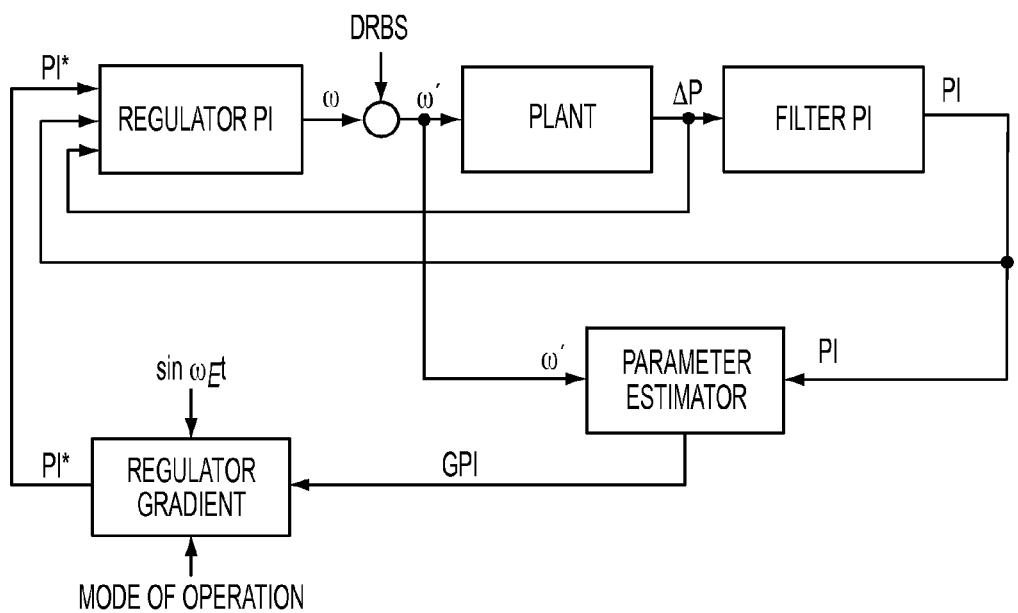
FIG. 6 is a schematic control loop, ω, pump speed; Δp, pressure difference; PI, pulsatility index; PI*, reference PI; GPI, gradient of PI with respect to ω; DRBS, discrete random binary signal; $ω_E$, auxiliary sinusoidal signal.

A cascaded control loop was designed (FIG. 6). The outer loop regulates the GPI according to the selected operating mode. A parameter estimation algorithm calculates the current GPI using present and past values of the plant input $\omega'$ and plant output PI, where $\omega'$ is the reference pump speed $\omega$ superimposed with an auxiliary discrete random binary signal (DRBS) of small amplitude. The process is assumed to be linear in the vicinity of the current operating point and to be time-varying. The linear time invariant discrete-time difference equation of an ARX process model of order tri and delay d is given by $$y(k)+a_1 y(k-1)+\ldots+a_m y(k-m)=b_1 u(k-d)+\ldots+b_m u(k-d-m)+e(k) \quad (6)$$

with inputs $u=\omega$, outputs $y=PI$ and equation error e which must be assumed to be white noise. A recursive least square (RLS) method estimates the system parameters $a_1 \ldots a_m$ and $b_1 \ldots b_m$ on-line. The GPI can be calculated as the plant gain:

$$GPI = \frac{\sum_{k=1}^{m} b_k}{1+\sum_{k=1}^{m} a_k}. \quad (7)$$

The system parameters may vary slowly or rapidly with time. Slowly time-varying parameters can be tracked with a constant forgetting factor approach with sufficiently low parameter variance. This may be the case for gradual changes of venous return, afterload or contractility. Rapidly varying or jumping systems, however, require special algorithms to allow fast tracking without sacrificing smoothness of the estimates. A sudden change of venous return may occur during a change of body posture and when straining or coughing. A time-varying forgetting factor approach which is controlled by the a-posteriori variance of the estimation error was used.

Figure 7:
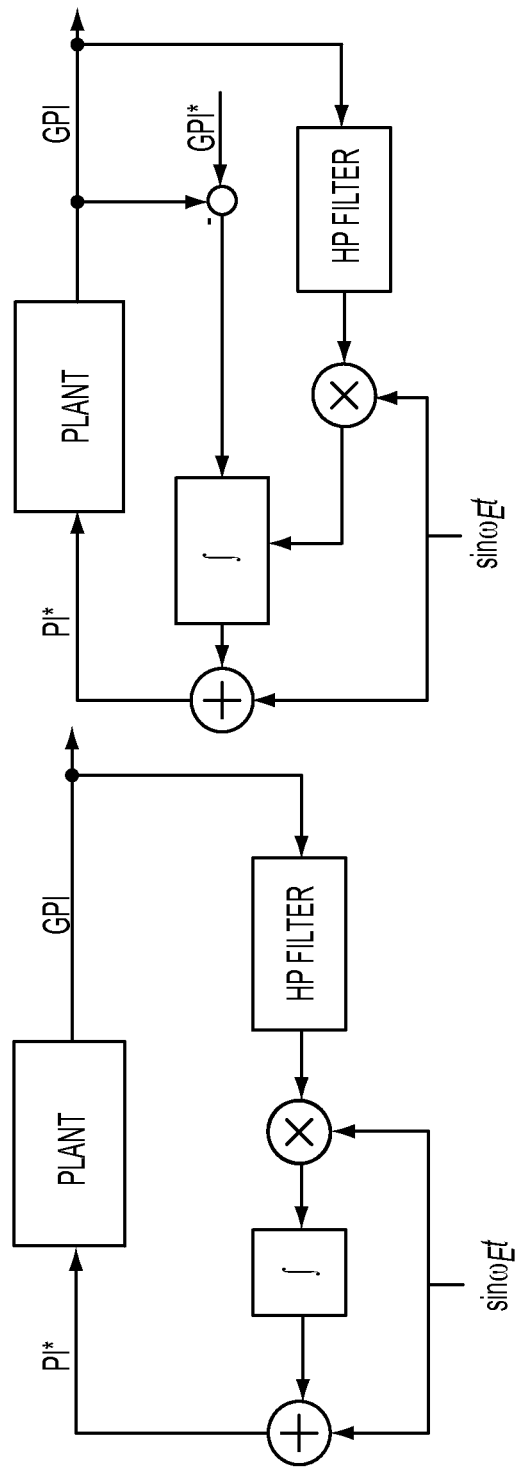
FIG. 7 is a block diagram of GPI control (outer control loop) Left: extremum seeking control for mode FA; Right: Reference tracking control with gradient information. HP, high-pass; ∫, integrator; $ω_E$, auxiliary sinusoidal signal; Plant, pump with left heart and adjacent vasculature.

Extremum-seeking control (ESC) is employed for controlling the GPI (FIG. 7). ESC minimizes the objective function $GPI=f(\omega)$. As $GPI(\omega)$ is a convex function for $GPI<0$ (see FIG. 3, bottom), the minimum can be found. ESC relies on auxiliary excitation of the plant input signal $\omega$. The cascaded controller as shown in FIG. 6 however, allows no direct manipulation of $\omega$ by the gradient controller. Instead, the reference value PI* must be used to impose the required excitation signal. As $PI=f(\omega)$ is a monotonically falling function for $GPI<0$, $GPI=f(PI)$ is also a convex function. The excitation signal is a sine wave with low frequency and amplitude. This signal is also used to demodulate the high-pass-filtered plant output to extract the gradient information which is then fed into an integrator. The output of the integrator approaches the PI* value for which GPI is at a minimum (i.e. $\delta GPI/\delta PI=0$).

In PA mode, the current estimate of the GPI is kept at a constant negative reference value (e.g. −3 mmHg·min) by an integral controller. The ESC is merely used to extract gradient information to detect the falling slope of the function $GPI=f(\omega)$ (which corresponds to the rising slope of $GPI=f(PI)$). If an incorrect slope is detected, the mode is temporarily switched to FA until the extremum is found. Following a further increase of PI* (reduction of $\omega$) the mode is switched back to PA mode.

Figure 8:
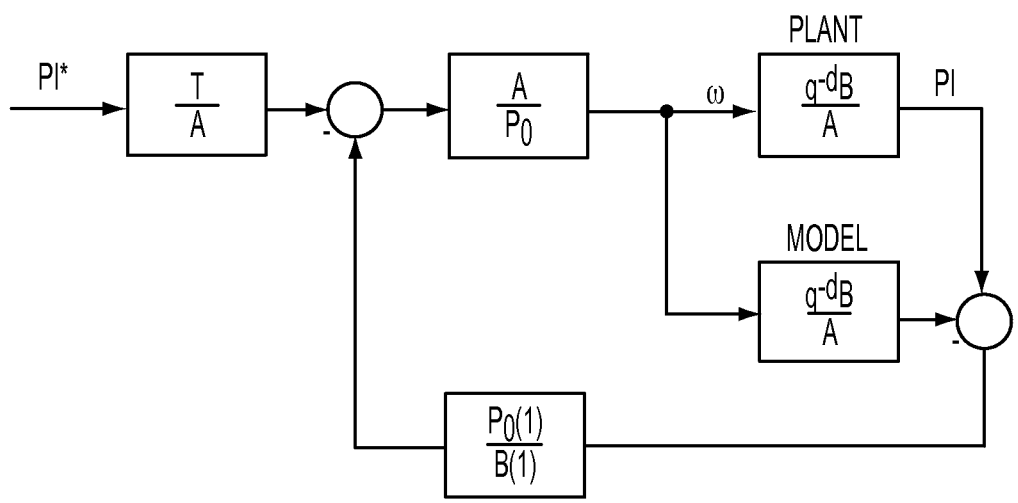
FIG. 8 shows a schematic of inner control loop for regulation of PI.

Adverse pumping states such as suction and regurgitation can be detected on the basis of non-negative GPI estimates and are corrected by the controller. The output PI* of the gradient controller is the reference signal for the inner control loop (FIG. 8). A predictive controller was designed using the Internal Model Control (IMC) scheme. The plant in (6) may be written $$A(q^{-1})y(t)=q^{-d}B(q^{-1})u(t) \quad (8)$$

with the polynomials $A(q^{-1})=1+a_1 q^{-1}+\ldots+a_m q^{-m}$ and $B(q^{-1})=b(q^{-1})=b_{1q}^{-1}+\ldots+b_m q^{-m}$. The transfer function can be derived from Eq. 8

$$G(q^{-1}) = \frac{q^{-d}B(q^{-1})}{A(q^{-1})}. \quad (9)$$

The closed-loop poles P contain the poles of the plant A and the auxiliary poles $P_0$:

$$P(q^{-1})=A(q^{-1})P_0(q^{-1}). \quad (10)$$

Polynomial T is used to design the tracking dynamics. Polynomials T and $P_0$ were properly tuned to yield robust stability and performance for varying plant gains (i.e. varying GPI).

The behavior of the entire control loop was tested in simulations for various combinations of physiological parameters. Unless otherwise stated, a typical parameter set was used as a standard for all following simulations: $E_{max}$=1 mmHg/ml, AoP=85 mmHg, $p_{ven}$=4 mmHg and heart rate=90 bpm.

Figure 9:
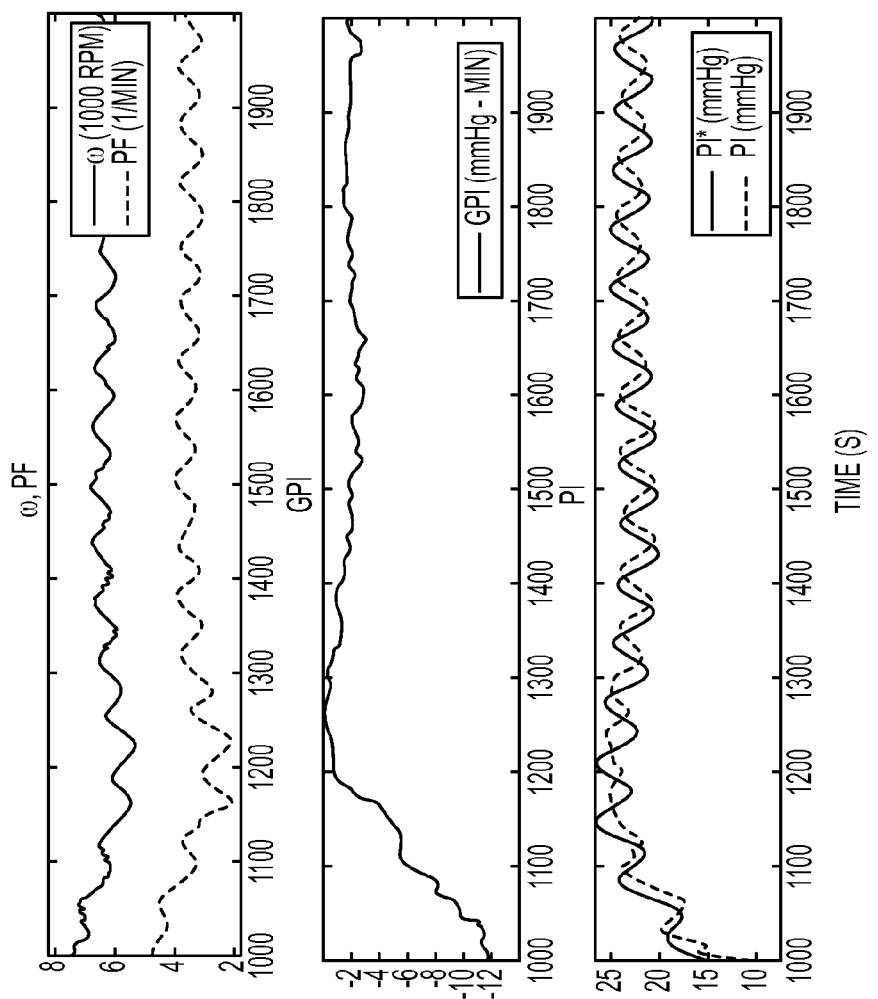
FIG. 9 shows the transition from mode FA to mode PA.
Figure 10:
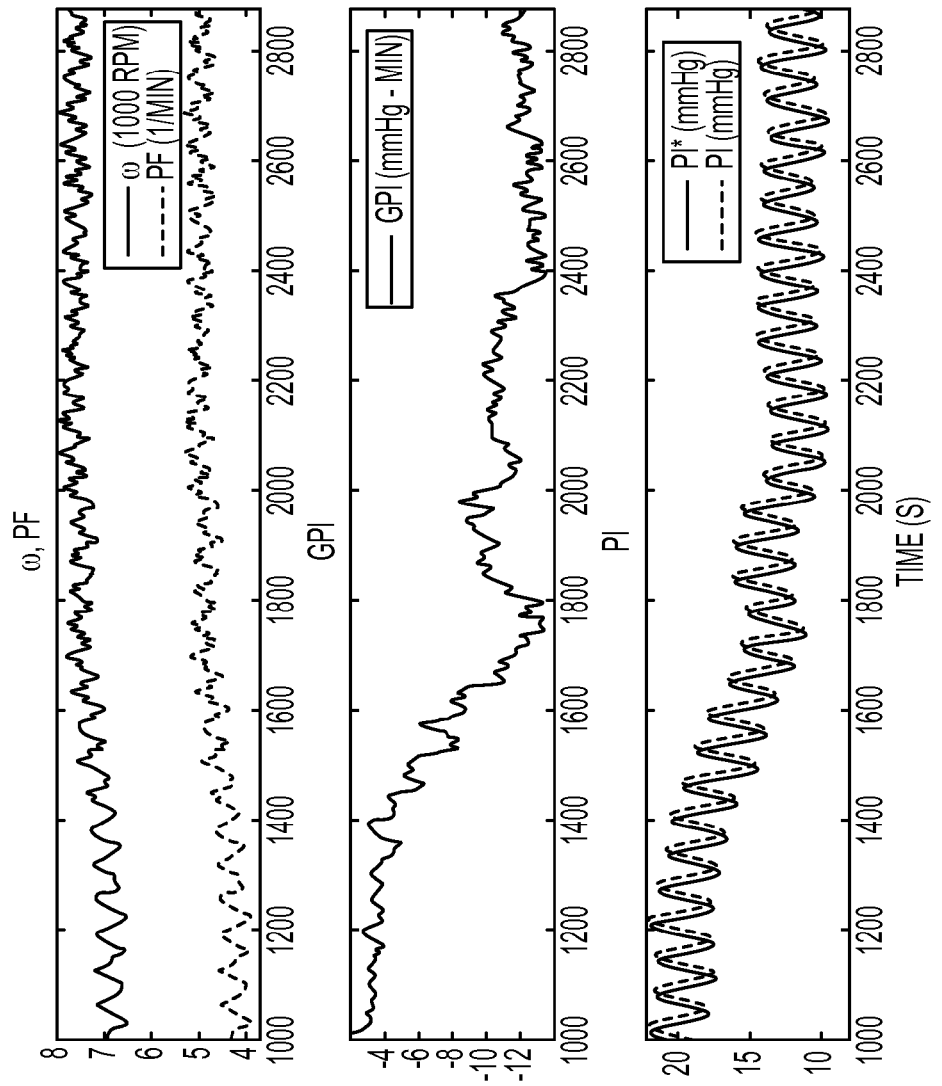
FIG. 10 shows the transition from mode PA to mode FA.
Figure 11:
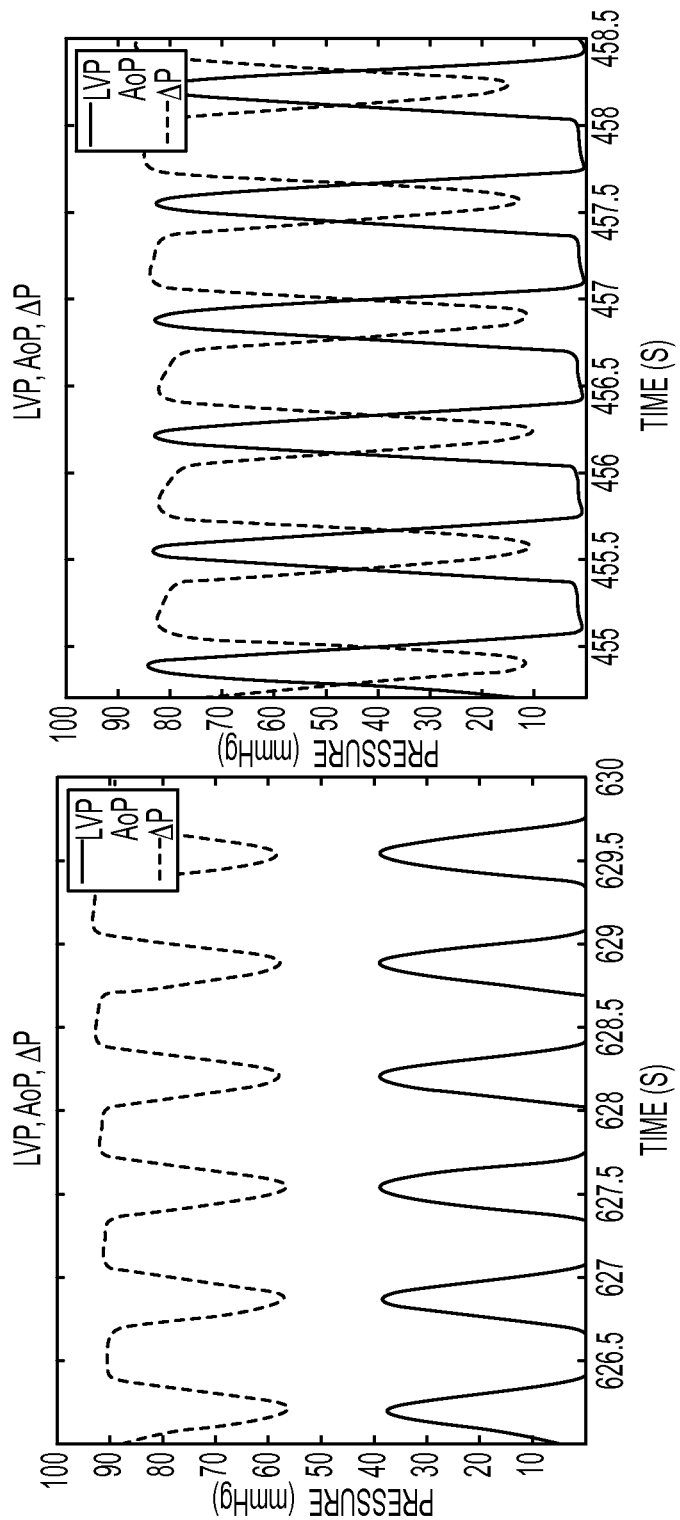
FIG. 11 shows pressure waveforms for both operation modes. Left: Mode FA; Right: Mode PA.

Simulations were carried out for both modes of operation. FIG. 9 shows the transition from mode FA to PA to demonstrate the performance of the outer control loop for GPI control. The GPI changes from −11 mmHg·min to the required −3 mmHg·min within 500 s. Within the same time, PI rises from 12 mmHg to 22 mmHg, ω decreases from 7700 rpm to 6400 rpm and PF decreases from 5.0 l/min to 3.5 l/min. Note that the reduction of PF in a patient would force $p_{ven}$ to rise, causing a recovery of PF at the expense of a higher left-ventricular volume (LVV) and higher LAP. In the simulation, however, $p_{ven}$ has been kept constant. FIG. 10 shows the transition back to FA. GPI, PI, ω and PF revert to their original values. This transition takes roughly 1000 s. In both operating modes, the gradient control loop was stable. The oscillations of PI, ω and PF are caused by the sinusoidal excitation for ESC. In FA mode, the level of PF was high enough to keep the LVV in a range where the LVP stays well below the aortic pressure (FIG. 11, left). In PA mode, the LVP briefly reaches the level of AoP which allows the AoV to open (FIG. 11, right). The peak LVP oscillates periodically due to the sinusoidal excitation.

Figure 12:
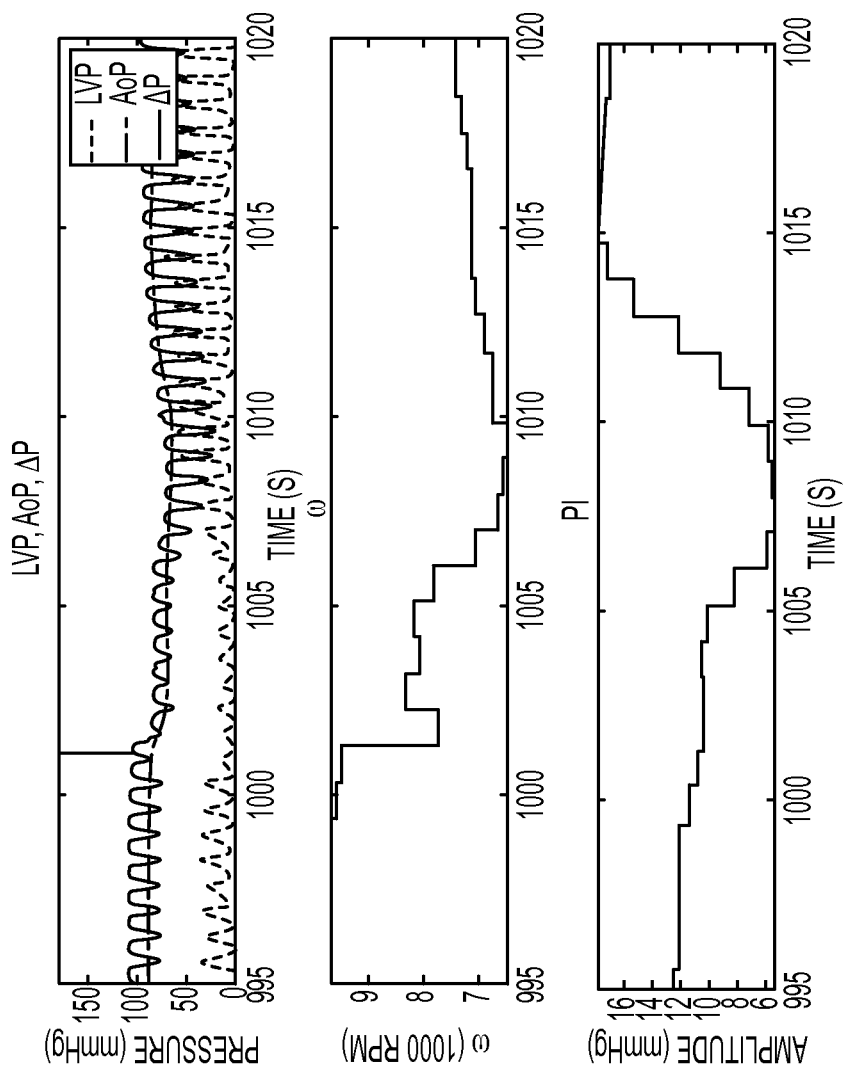
FIG. 12 is a transient response to a step decrease of $p_{ven}$.

The reaction of the inner control loop to sudden changes in venous return is simulated by a stepwise decrease of $p_{ven}$ from 6 mmHg to 4 mmHg (FIG. 12). FA mode is the more demanding test case because the safety margin to the suction point is smaller than in PA mode. The pulse amplitude of the Δp signal drops to zero within 2 heart beats. One suction spike occurs before ω is rapidly reduced and further suction spikes can be avoided. The PI recovers within 10 s and increases to above the initial value. After another 15 s (not shown in FIG. 12), the PI returns to the initial value. The pump speed decreases from 9660 rpm to 7375 rpm. In PA mode (not shown), no suction spikes occur during a step decrease of $p_{ven}$.

Preload-based control of RBP is the most common control method used for clinically available pumps as well as for investigational devices. Preload is reflected in the pulsatility of the PF, Δp or motor current signal, provided that the LV demonstrates some residual contractility. Methods based on maintaining a predetermined PI reference level demonstrated a lack of adaptation to changing physiological variables such as contractility or afterload since the level of PI is affected by these variables. Consequently, the adjusted reference value for the PI is optimal only for one particular parameter set. If contractility increases, for instance, the PI would have to be increased too. There are several approaches to address this problem. It may be possible to propose a manipulation of the pump speed to verify whether some characteristics as PI, pump flow and power consumption behave as expected. As a result of the speed changes, the reference value for PI is increased when there is an imminent risk of suction, or otherwise decreased. Our proposed control method is also based on the application of speed variations for evaluating the reaction of the system. We continuously obtain an estimate of the GPI which can be used to fulfil different control purposes by simply controlling the GPI in an appropriate way.

Several proposed control methods aim to adaptively operate the pump at a point where the flow rate is maximal. It may be possible to increase the pump speed until the point of suction is detected and subsequently decrease the pump speed. This approach has been further investigated by the same group. A method based on ESC has been proposed to maximize either the mean PF or the PF during diastole. Consequently, the pump is operated near the collapse point of the LV. To increase the safety margin to the suction point, slope-seeking control, as a special case of ESC, has been proposed in order to operate the pump at a slightly higher degree of LVV. Similarly, it might be tried to use own nor pressure pulsatility on its own as a control variable, but rather the quotient of these two parameters. This index will decrease at induction of suction and can thus discriminate between pulsatility caused by LV contraction and suction. All these methods have in common that the pump is operated near the onset of suction. Occasional occurrence of suction is even tolerated. It is our opinion, however, that suction has to be avoided under all circumstances. Unlike the strategies outlined above, we propose to operate the pump in FA mode at a speed where ventricular collapse is unlikely due to the larger safety margin towards suction. It is not necessary to test for the onset of suction and suction can therefore be avoided.

In contrast to the high-flow operating point, with our PA mode, we additionally propose a method which can operate the pump at a point where the degree of unloading is not maximal, but where the LV filling is more physiological and ventricular washout is optimized due to better LV wall movement. We defined this point to be in the transition region between the point where the aortic valve opens and that point where it is permanently closed. This operating point is often selected manually by the physician, either with echocardiographic guidance or by interpreting the pressure difference waveform. This region can be detected quite precisely using the gradient information of PI with respect to pump speed (GPI), provided that the residual contractility of the LV is high enough at all to enable ejection through the AoV at low pump speeds. However, the GPI is not readily available when the pump is operated at one specific speed. It can be estimated with parameter estimation methods based on observation of input-output data over a certain time interval. For proper excitation of the system, an auxiliary signal (DRBS) has to be added to the input. The resulting speed changes are not expected to be perceived by the patient. We applied ESC to control the GPI. ESC also needs an auxiliary signal which has a much lower frequency but a higher amplitude than the DRBS. The resulting low-frequency oscillation might be a drawback of this method, but has the positive side effect that in PA mode the AoV will open during low-speed phases and stay closed during high-speed phases. The rather long response time of the ESC is based on the recursive estimation time. The gradient control loop determines the proper reference signal for control of PI. This reference point has to be modified according to the changing physiological parameters. Changes of $E_{max}$ require the largest corrections of the reference point (see FIG. 4), followed by changes of AoP (see FIG. 5). As the contractility is not expected to change suddenly, the adaptation velocity of the controller is believed to be adequate. Changes in AoP caused by changes of the systemic vascular resistance (SVR) are usually ramp-like changes. If, for example, the AoP decreases too fast for the PI* follow suit when in PA mode, pump speed will temporarily decrease until the controller reacts by decreasing PI*. The fastest changes are expected for $p_{ven}$. However, PI* can be kept almost constant for altering $p_{ven}$ (see FIG. 3).

Sudden changes in $p_{ven}$ are handled instead by the inner control loop. The applied IMC scheme, as a special case of pole placement strategy, is a simple control structure which has the advantage of an easy design of the closed-loop poles to achieve fast regulation dynamics without overshoot. If the closed-loop dynamics are not faster than the open loop dynamics, the IMC scheme inherently offers a convenient way to ensure predictable behavior in the presence of input constraints (speed limits of the pump). The response to output disturbances is fast enough to avoid collapse of the LV. In FA mode, only one suction spike occurs when the venous return is suddenly reduced. Such a fast transient has not been observed in any patient according to the INCOR patient data base. Generally, the pulse amplitude does not drop to zero any faster than within 5 consecutive heart beats. Hence, the simulated reduction within 2 heart beats can be regarded as being the worst case. Almost no overshoot has been observed, neither for reference nor for output step responses at different values for GPI. The fast dynamics of the IMC had to be traded against a slow reaction during arrhythmias. Although good robustness against arrhythmias is anticipated due to the use of time-averaging algorithms rather than pattern recognition methods, tests with various forms of arrhythmia still have to be carried out.

The physician is given the option of selecting between full assist and partial assist. The reduction to just two distinct options may seem draconic, but the objective is to relieve the physician from having to make decisions on to many poorly-known variables.

Figure 13:
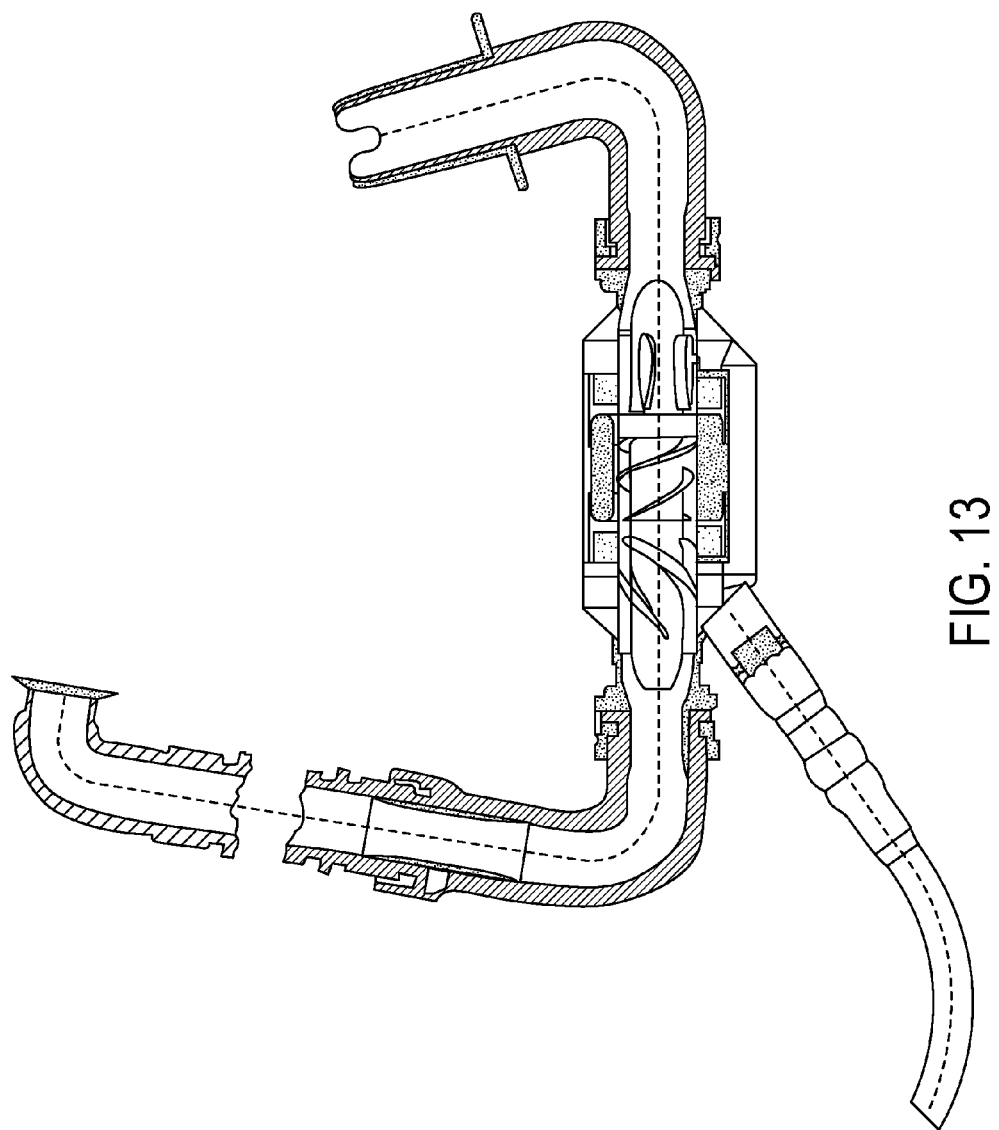
FIG. 13 is a rotational blood pump.

For a deeper understanding of the invention's rotational pump. FIG. 13 shows a schematic view of a rotational pump.

Figure 14:
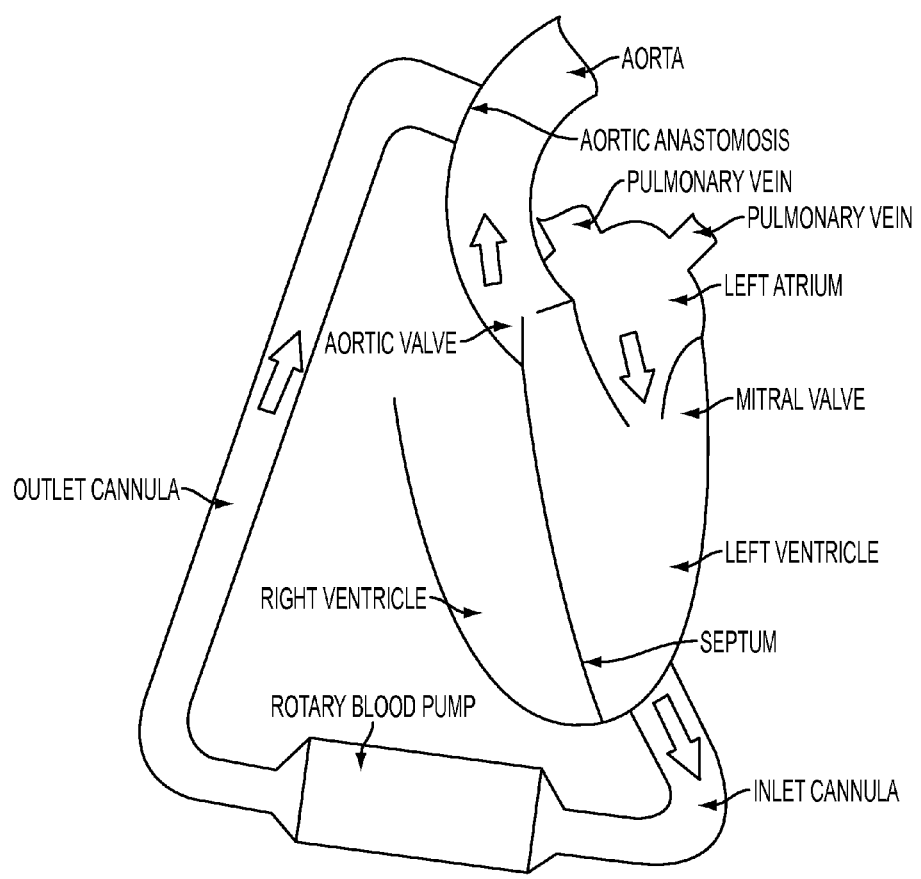
FIG. 14A rotational blood pump connected to a human heart.

FIG. 14 shows this pump connected to a human heart.

The invention claimed is:

1. A method to control a rotational blood pump operating at a rotational speed comprising:
   selecting a user-selectable control objective from at least two control objectives;
   measuring at least one of a pressure, a pressure difference or a flow rate;
   regulating the pump to an operating point satisfying the selected control objective by modifying the rotational speed of the pump based on the at least one of the pressure, the pressure difference or the flow rate,
   calculating an index of pulsatility from the pressure difference or the flow rate; and
   controlling the index of pulsatility to a set point based on a gradient of the index of pulsatility,
   wherein the modifying the rotational speed of the pump comprises the regulating the index of pulsatility, and
   wherein the rotational speed of the pump is temporarily reduced from the operating point to allow an aortic valve or a pulmonary valve to open in systole.

2. A method to control a rotational blood pump operating at a rotational speed comprising:
   selecting a user-selectable control objective from at least two control objectives;
   measuring one of a pressure, a pressure difference and a flow rate; and
   regulating the pump to an operating point satisfying the selected control objective by modifying the rotational speed of the pump based on the measured one of the pressure, the pressure difference and the flow rate,
   wherein an index of pulsatility is calculated and the index of pulsatility is calculated from the pressure difference or flow rate, and
   wherein the index of pulsatility is set to a reference value depending on a gradient of the index of pulsatility.

3. The method according to claim 2, wherein the operating point corresponds to the reference value of the gradient of the index of pulsatility, said gradient being selected in such a way that the pump operates in a transitional phase in between an opening and a closing of an aortic valve or a pulmonary valve.

4. The method of claim 2, wherein the gradient of the index of pulsatility is determined by means of random speed variations and a recursively amended model.

5. The method of claim 2, wherein a model for calculating the gradient of the index of pulsatility is used, which is adapted with a changing rate that depends on a patient's activity.

6. The method of claim 2, wherein the gradient of the index of pulsatility is controlled to its minimum by an extremum controller.

7. The method of claim 2, wherein modifying the rotational speed of the pump is based on the index of pulsatility and the measured one of the pressure, the pressure difference and the flow rate.

8. A method to control a rotational blood pump operating at a rotational speed comprising:
   selecting a user-selectable control objective from at least two control objectives;
   measuring one of a pressure, a pressure difference and a flow rate;
   regulating the pump to an operating point satisfying the selected control objective by modifying the rotational speed of the pump based on the measured one of the pressure, the pressure difference and the flow rate,
   calculating an index of pulsatility from the pressure difference or the flow rate; and
   setting a reference value of the index of pulsatility depending on a gradient of the index of pulsatility,
   wherein the operating point is selected in such a way that the pump operates in a transitional phase in between an opening and a closing of an aortic valve or a pulmonary valve.

9. The method according to claim 8, wherein the control objectives include a partial assist mode and a full assist mode.

10. A method to control a rotational blood pump operating at a rotational speed comprising:
    selecting a user-selectable control objective from at least two control objectives;
    measuring at least one of a pressure, a pressure difference or a flow rate;
    regulating the pump to an operating point satisfying the selected control objective by modifying the rotational speed of the pump based on the at least one of the pressure, the pressure difference or the flow rate,
    calculating an index of pulsatility from the pressure difference or the flow rate, and
    wherein regulating the pump to the operating point comprises regulating the index of pulsatility to a reference value based on a gradient of the index of pulsatility,
    wherein a preload-based control is used to verify whether a pre-defined set-point is to be increased or decreased.

11. A control system for controlling a rotational pump capable of running at a rotational speed, the control system comprising a measuring system coupled to the pump for direct or indirect measurement of at least one of a pressure, a pressure difference or a flow rate across the pump, the control system configured to regulate the pump to an operating point,
    wherein the operating point is selected such that the pump operates in a transition region between an opening and a closed aortic valve, the region being at a transition point between a full assist mode and a partial assist mode,
    wherein the control system is configured to temporarily reduce the rotational speed of the pump in the transitional region by or to a fixed value to allow an aortic valve or a pulmonary valve to open in systole, wherein the control system is configured to calculate an index of pulsatility from the pressure difference or the flow rate, and wherein the control system is configured to temporarily reduce the rotational speed of the pump in the transitional region based on a regulation of the index of pulsatility to a reference value, wherein the regulation of the index of pulsatility is dependent on a gradient of the index of pulsatility.

12. The control system of claim 11, wherein the control system is configured to temporarily reduce the rotational speed of the pump in the transitional region by the fixed value to allow the aortic valve or the pulmonary valve to open in systole.

* * * * *